(12) United States Patent
Lichtenstein et al.

(10) Patent No.: US 8,444,635 B2
(45) Date of Patent: May 21, 2013

(54) METHODS FOR SELECTIVELY HEATING TISSUE

(76) Inventors: Samuel Victor Lichtenstein, Vancouver (CA); Daniel Gelbart, Vancouver (CA)

(*) Notice: Subject to any disclaimer, the term of this patent is extended or adjusted under 35 U.S.C. 154(b) by 483 days.

(21) Appl. No.: 12/590,807

(22) Filed: Nov. 16, 2009

(65) Prior Publication Data
US 2010/0125271 A1 May 20, 2010

Related U.S. Application Data

(60) Provisional application No. 61/193,334, filed on Nov. 19, 2008.

(51) Int. Cl.
*A61B 18/18* (2006.01)
(52) U.S. Cl.
USPC .............................. 606/33; 607/101
(58) Field of Classification Search
USPC ............... 606/17, 18, 33, 34; 607/90, 91, 94, 607/100, 101, 142, 148
See application file for complete search history.

(56) References Cited

U.S. PATENT DOCUMENTS

| | | | |
|---|---|---|---|
| 3,927,557 A * | 12/1975 | Viertl | 73/607 |
| 4,298,009 A * | 11/1981 | Mezrich et al. | 600/443 |
| 4,632,127 A | 12/1986 | Sterzer | |
| 5,010,897 A * | 4/1991 | Leveen | 607/101 |
| 5,117,829 A | 6/1992 | Miller et al. | |
| 5,451,221 A * | 9/1995 | Cho et al. | 606/3 |
| 5,571,154 A | 11/1996 | Ren | |
| 6,328,689 B1 | 12/2001 | Gonzales et al. | |
| 6,428,532 B1 * | 8/2002 | Doukas et al. | 606/9 |
| 6,610,043 B1 | 8/2003 | Ingenito | |
| 6,613,005 B1 | 9/2003 | Friedman et al. | |
| 6,692,494 B1 | 2/2004 | Cooper et al. | |
| 6,709,401 B2 | 3/2004 | Perkins et al. | |
| 6,712,816 B2 | 3/2004 | Hung et al. | |
| 6,997,918 B2 | 2/2006 | Soltesz et al. | |
| 7,004,940 B2 | 2/2006 | Ryan et al. | |
| 7,300,428 B2 | 11/2007 | Ingenito | |
| 7,412,977 B2 | 8/2008 | Fields et al. | |
| 7,587,230 B2 * | 9/2009 | Litovitz | 600/409 |
| 7,770,584 B2 * | 8/2010 | Danek et al. | 128/898 |
| 2003/0018327 A1 | 1/2003 | Truckai et al. | |
| 2004/0047855 A1 | 3/2004 | Ingenito | |
| 2005/0038339 A1 | 2/2005 | Chauhan et al. | |
| 2005/0085801 A1 | 4/2005 | Cooper et al. | |
| 2005/0281800 A1 | 12/2005 | Gong et al. | |
| 2006/0047291 A1 | 3/2006 | Barry | |
| 2006/0135947 A1 | 6/2006 | Soltesz et al. | |
| 2006/0161233 A1 | 7/2006 | Barry et al. | |
| 2006/0259103 A1 * | 11/2006 | Stenzel | 607/101 |
| 2007/0043350 A1 | 2/2007 | Soltesz et al. | |
| 2008/0033412 A1 * | 2/2008 | Whelan et al. | 606/11 |

(Continued)

*Primary Examiner* — Linda Dvorak
*Assistant Examiner* — Jocelyn D Ram
(74) *Attorney, Agent, or Firm* — Oyen Wiggs Green & Mutala LLP

(57) ABSTRACT

The invention can selectively heat a diseased area or undesired tissue in the body while minimizing heating to the healthy area and surrounding tissue. This is done by exposing the undesired tissue to a scanning focused microwave beam arriving from different directions, all directions passing through the undesired tissue. The invention is particularly useful for heating tissues in which the undesired tissue has reduced blood flow. The undesired area will heat up rapidly while the healthy tissue will be cooled by the blood flow. This is particularly effective for treating emphysema because of the low mass of the lungs and the high blood flow.

12 Claims, 4 Drawing Sheets

U.S. PATENT DOCUMENTS

| | | |
|---|---|---|
| 2008/0097139 A1* | 4/2008 | Clerc et al. .................. 600/7 |
| 2008/0132826 A1 | 6/2008 | Shadduck et al. |
| 2008/0167555 A1 | 7/2008 | Qian et al. |
| 2008/0228137 A1 | 9/2008 | Aljuri et al. |
| 2008/0249503 A1* | 10/2008 | Fields et al. ................ 604/506 |
| 2010/0042020 A1* | 2/2010 | Ben-Ezra ...................... 601/3 |
| 2010/0125225 A1* | 5/2010 | Gelbart et al. ................ 601/3 |
| 2012/0089209 A1* | 4/2012 | Schoenbach et al. ........ 607/100 |

* cited by examiner

METHODS FOR SELECTIVELY HEATING TISSUE

CROSS REFERENCE TO RELATED APPLICATIONS

This application claims the benefit under 35 U.S.C. §119 of U. S. patent application Ser. No. 61/193,334 filed on 19 Nov. 2008 and entitled A SYSTEM FOR TREATING UNDESIRED BODY TISSUE.

FIELD OF THE INVENTION

The invention relates to the medical field and in particular to the treatment of emphysema.

BACKGROUND OF THE INVENTION

In many diseases it is desired to destroy or affect a non-desired tissue without harming the adjacent normal tissue. A non surgical approach has many advantages, such as shorter recovery time. Common non surgical approaches are:

Radiation therapy using X-ray or radioactive materials.
RF or microwave ablation using a probe applied from the outside or inside of the body, with or without cooling.

Examples of the need for such non-surgical procedure are the destruction of tumors, shrinking of an enlarged prostate and collapsing of diseased parts of a lung affected by emphysema. In a patient suffering from emphysema, the diseased parts can not easily ventilate through the bronchi and trachea, thus preventing the lung from fully deflating and inflating. The trapped air does not allow the diaphragm to move up and down naturally. If the diseased area can be mildly heated, its ability to produce a surfactant coating and other chemicals can be greatly reduced. This allows one to collapse the diseased area by collapsing the whole lung and re-inflating it. The healthy tissue will inflate while the diseased area will stay as a compressed lump. This will allow the diaphragm to move naturally and force air in and out of the healthy lung tissue. This procedure is well known in pulmonary medicine. Background on lung disease can be found in medical textbooks, such as "Pulmonary Pathophysiology" by Dr. John B. West, ISBN 0-683-08934-X. Prior art approaches to heat the diseased parts of the lung involve inserting an ablation device through the trachea and bronchi. This approach has two major shortcomings: only a small part of the lung is accessible, and precise mapping of the diseased area is required, as well as precise location of the ablation device. It is desired to have a system that automatically heats the diseased area without having to locate it precisely. It is also desired to be able to heat all diseased parts of the lung without excessively heating the healthy parts or the surrounding tissue. These and other objectives are achieved by the present invention.

SUMMARY OF THE INVENTION

The invention can selectively heat a diseased area or undesired tissue in the body while minimizing heating to the healthy area and surrounding tissue. This is done by exposing the undesired tissue to a scanning focused microwave beam arriving from different directions, all directions passing through the undesired tissue. The invention is particularly useful for heating tissues in which the undesired tissue has reduced blood flow. The undesired area will heat up rapidly while the healthy tissue will be cooled by the blood flow. This is particularly effective for treating emphysema because of the low mass of the lungs and the high blood flow.

DETAILED DISCLOSURE

One aspect of the invention uses the fact that healthy lung tissue has much larger blood circulation than diseased tissue such as a lung affected by emphysema. When a non-contact heat source, such as microwave energy, is directed at the lung the heat will be carried away from the healthy tissue by the blood flow while the diseased parts of the lung will heat up. When diseased tissue is heated up to around 60 deg C. it loses the ability to expand back after lungs are collapsed, because of damage to the surfactant layer and other physiological reasons. Causing the areas affected by emphysema to collapse prevents them from interfering with normal operation of the healthy parts of the lung, similar to what can be achieved by surgically removing the diseased part. The reason this procedure is effective on the lungs is that the mass of the lungs is low (about 1 Kg) while the blood flow through the lung is high (about 5 Kg/minute) and the blood flow tends to equalize the temperature of the healthy part of the lung with the rest of the body, representing a heat-sink of tens of kilograms. When lungs are exposed to a form of energy causing heating, such as microwave or ultrasonic energy, the amount of heating will be proportional to the heat-sinking mass. For a diseased lung it is typically below one Kg while for a healthy lung the heat transfer to the body represents a heat sink from 10 to 100 times larger. Based on this, when the diseased area will heat up to 50-70 degrees C., the healthy lung areas will only heat up a few degrees above normal body temperature. Another advantage of the method is that the location of the diseased area does not need to be precisely known: the heating energy can be directed at the whole lung, but only the diseased areas will heat up significantly. To assist in keeping down the temperature of the healthy parts of the lung, the patient can be breathing chilled air during the procedure. The diseased parts will not get a sufficient amount of chilled air to keep them cool. After heating the lung, an operation than can take seconds or minutes, the lung is collapsed by inserting a hypodermic needle into the pleural space, in order to allow air to leak into this space. Supplying the lung with pure oxygen will speed up the collapse as it is fully absorbed in the blood. After leaving the lung in a collapsed state long enough to allow the diseased area to collapse into a small volume, the lung is re-inflated by evacuating the pleural space via the same needle used to collapse the lungs. Obviously the procedure can be done on one lung at a time, as the patient can breathe with the remaining lung. The procedure of collapsing and inflating the lung is done routinely in pulmonary medicine and need not be detailed here.

Figure 1:
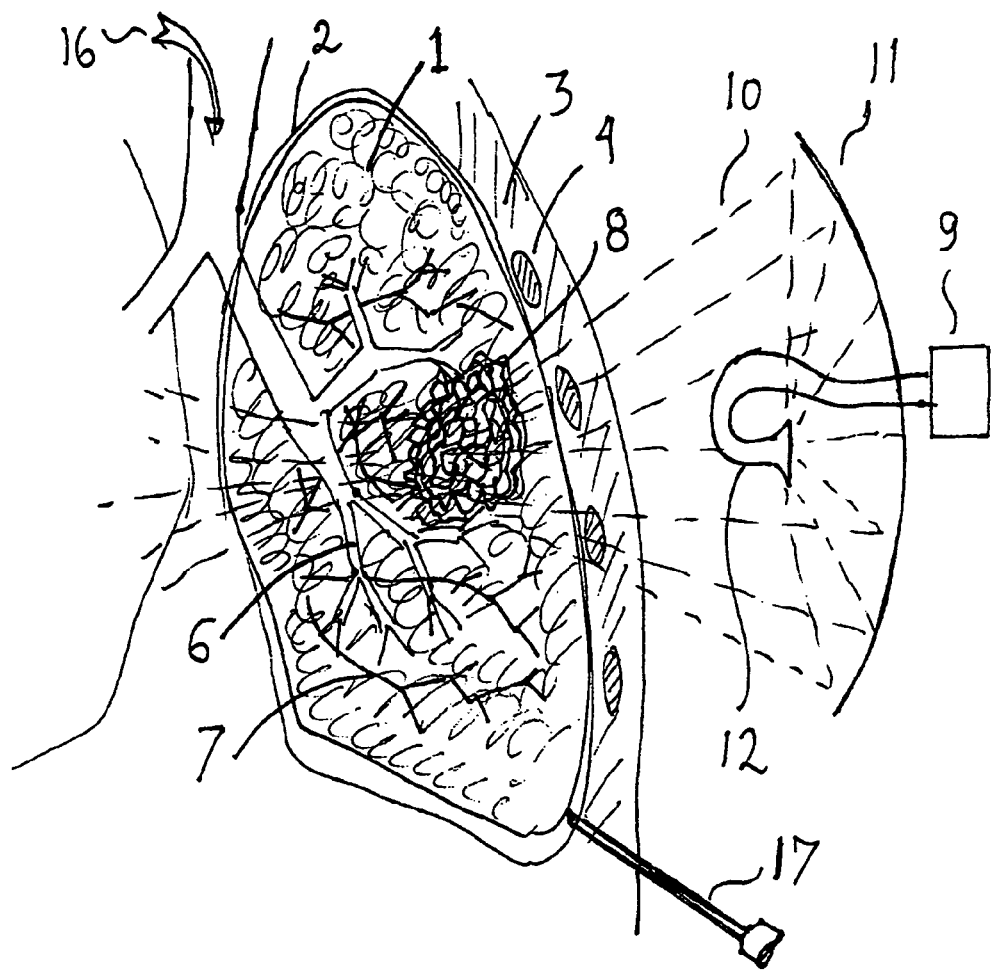
FIG. 1 is a cross section of a lung being exposed to directional microwave radiation.

FIG. 1 shows a cross section of a lung 1 in a pleural bag 2 ventilated via trachea 16 and bronchi 6. Blood is supplied by veins 7. The diseased area 8 has significantly lower blood supply. Microwave source 9 is coupled to antenna 11, typically a parabolic reflector, via feed horn 12. The art of directional microwave antennae is well known in radar and diathermy. The microwave radiation 10 penetrates the tissue 3 and ribs 4 and mainly heats up diseased area 8. After heating, lung 1 is collapsed via hypodermic needle 17 as explained earlier.

The size of the heated area inside the body has to be matched to the treated organ. In the case of lungs it is desired to have a heated spot of about 10 cm in diameter. The antenna size to achieve the desired spot size and depth of the zone having this size depends on the wavelength of the microwave used. It is easiest to express the relationship as a function of the f/# of the antenna, f/# being the ratio of the focal length to the diameter of the antenna. The size of the focused spot is approximately $(1.2) \times (f/\#) \times (\text{wavelength})$ and the depth of the focused zone is approximately $(3) \times (f/\#)^2 \times (\text{wavelength})$. The two most common microwave frequencies used for heating are 2.45 GHz and 915 MHz. The corresponding wavelengths in air are 12.2 cm and 33 cm. For a 10 cm diameter spot this will require about an f/1 antenna at 2.45 GHz and will be difficult to achieve at 915 MHz. It should be noted that the spot size in tissue is smaller than in air because of the dielectric properties of the tissue. More advanced beam shaping techniques can be used to improve these figures, as explained later. If ultrasound is used, achieving the spot size is easy. For example, using a large area piezoelectric transmitter having a diameter of 10 cm and operated at 1 MHz, the wavelength is about 1 mm and the natural diffraction angle is given by wavelength/diameter or 1 mm/100 mm=10 mR. In this case no focusing is required, the divergence of the ultrasonic beam will be about 10 mR. The disadvantage of ultrasonic heating is that it requires intimate coupling with the tissue. The heating methods described later on will have to be performed with the patient and the transmitter being submerged in water. Clearly scanning directions passing through sensitive organs can be eliminated by suitable programming of the system.

Another aspect of the invention is heating the diseased tissue while minimizing heating of the surrounding tissue, such as chest wall heating in the case of lung disease. This can be achieved by moving around the energy source in order for the heating to arrive from different directions. If all these directions pass through the diseased tissue, the diseased tissue will be heated continuously while the surrounding tissue will be heated intermittently. A similar method is employed today in radiation therapy for cancer, however using heat energy has a significant advantage: the effect or radiation, such as X-ray or radioactivity, is cumulative while the effect of heating is non-cumulative. Heating a tissue by 30 degrees will permanently change it, while heating it 10 times by 3 degrees will have no effect. In the case of radiation the effect will be cumulative.

Figure 2:
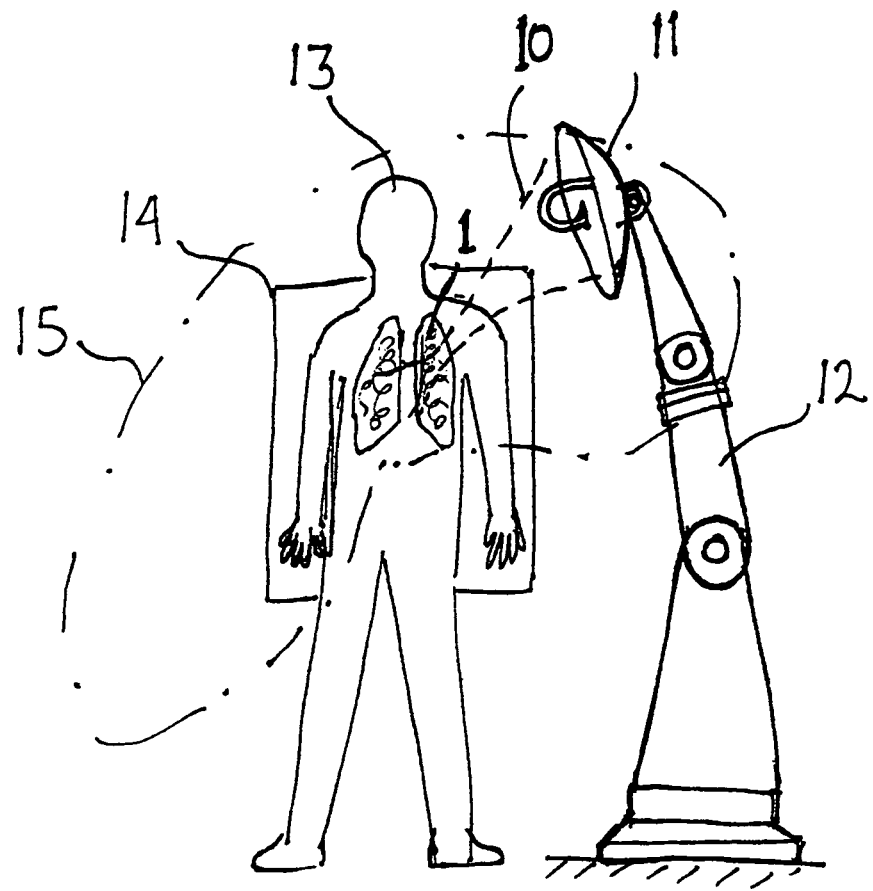
FIG. 2 is a schematic view of a microwave radiation treatment system using a robotic manipulator.
Figure 3:
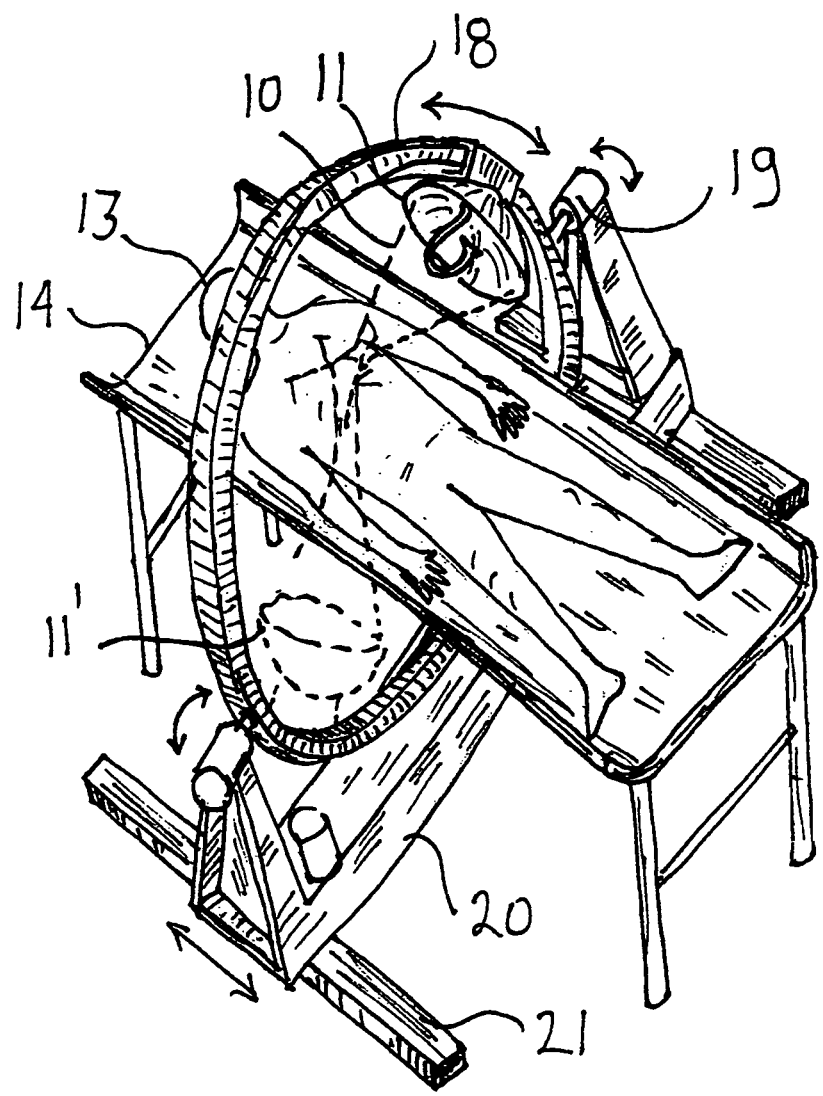
FIG. 3 is an isometric view of a microwave radiation treatment system using a circular track antenna manipulator.
Figure 4:
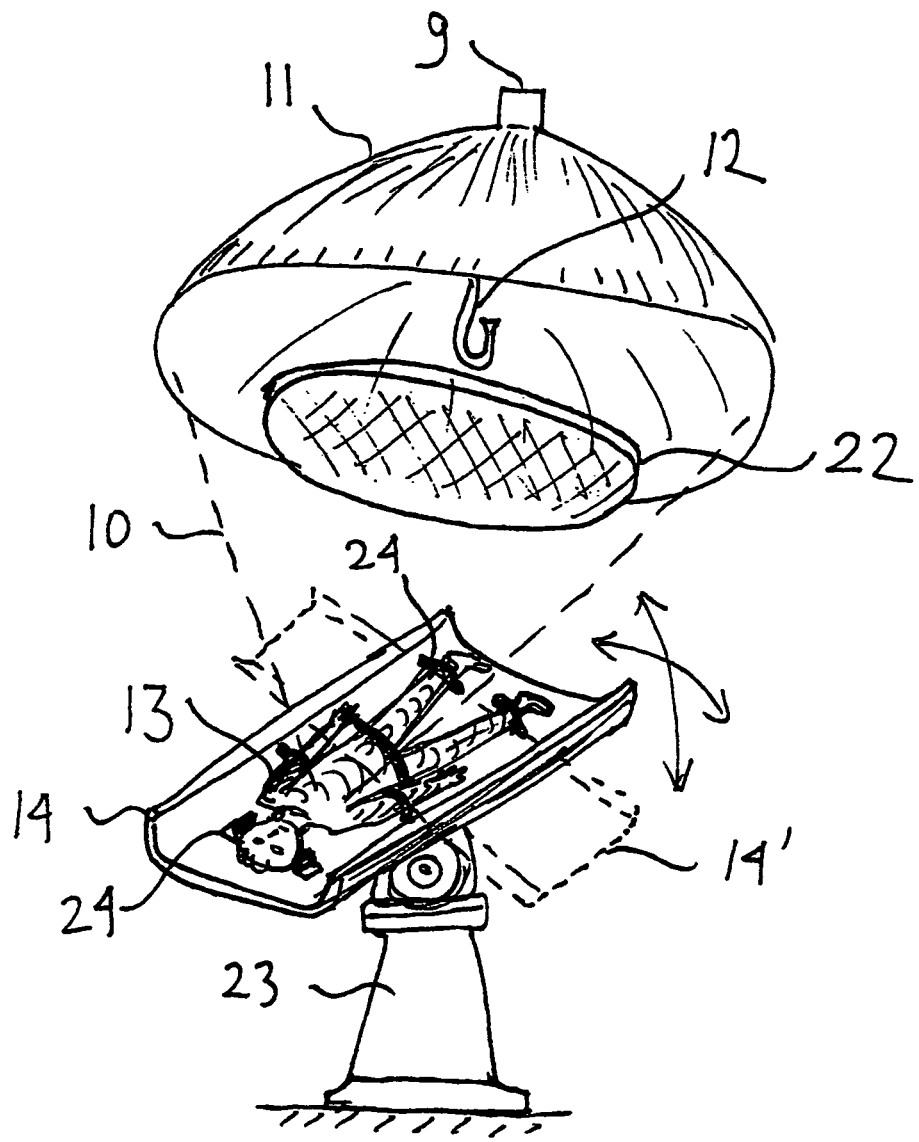
FIG. 4 is an isometric view of a microwave radiation treatment system using a stationary antenna and a patient manipulator.

One method of taking advantage of this non cumulative effect is shown in FIG. 2. A patient 13 is attached to a fixed reference frame 14. An antenna 11 is mounted on a robot arm 12 capable of moving the antenna around the patient in a 3D pattern while keeping the focus spot of beam 10 on lung 1. The trajectory of the antenna can be optimized to avoid passing radiation through sensitive organs such as the head, heart, spine etc. An alternate system is shown in FIG. 3. Patient 13 is immobilized on frame 14 while antenna 11 is moved around patient in track 18. Track 18 can be tilted by motors 19 mounted on frame 20. Frame 20 can be moved along the patient on track 21. This combination allows a 3D path, having the microwave energy reaching the lung from different direction but always staying focused on the lung. For example, when antenna 11 moves to position 11' the right side of the chest is being heated while the left side is cooling down, but the lung is being heated in both positions. The trajectory can be constantly changing and dwelling longer periods on less heat sensitive directions. As stated earlier, the patient can be further cooled by breathing chilled air. A coating (not shown) can be applied to the outside of the body to minimize reflection of the microwave energy and/or lower the skin temperature. Such a coating is known in the art of microwave as an "impedance match coating" and typically has an electromagnetic wave propagation velocity which is the geometric mean between velocities in tissue and air. Another option is shown in FIG. 4, in which the antenna 11 is stationary and patient 13 is immobilized to a frame 14 by restraints 24. Frame 14 can be tilted and rotated in all directions by robotic pedestal 23, as shown by new position 14'. This arrangement is suitable for large antennae or transmitters. Device 22 for reducing the size of the focused spot or other desirable beam shaping, such as increasing focal depth, can be added between antenna 11 and patient 13. A well known an example of such a device is an apodizing plate. For example a plate approximately half the diameter of antenna 11 and introducing a phase shift of 180 degrees. Such a plate reduces the size of the spot somewhat and greatly increases the depth of focus (by a factor of about 3). Another beam shaping device is disclosed in U.S. Pat. No. 5,571,154, hereby incorporated by reference.

This patent used an array of conductive spheres embedded in a low loss dielectric plate to shape the beam. Beam shapers causing side-lobes to the focal spot can be used, as the heat of these side-lobes will dissipate due to the non-cumulative nature of heating. Similar techniques to those discussed above can be used with other energy sources such as ultrasonic transducers, with patient and transducer submerged in a water bath. For lung heating the power transmitted to the body is typically in the range of 50 W to 1000 W. For heating smaller organs, such as a cancer site or the prostate, less power can be used, proportional to the mass of the target tissue. In general the beneficial reaction does not have to be limited to heating but any non-cumulative process has an advantage over a cumulative one. While microwave and ultrasound were used as an example of generating selective heating the invention is not limited to any particular source of energy. By the way of example RF, light, shockwaves and other energy sources can be used. In some cases the same system can be used as an imaging system, by reducing the power below the amount capable of ablation and measuring the reflection or absorption. Ultrasound based systems are particularly suitable for imaging and ablation.

While curing emphysema was given as an example, the invention can be used to heat other diseased or undesired tissue with minimal damage to adjacent tissue. For small organs such as a prostate, ultrasound is preferred to microwave. For cancer either one can be used. Both are used today but coming from a fixed direction, thus limited by the heating of the tissues they have to go through. By utilizing the 3D scanning as disclosed here, much more selective results can be achieved. By the way of example, a 10 cm diameter phased array piezoelectric transducer operation between 100 KHz and 1 MHz can form a focused spot of about 1 cm inside the prostate and can be moved around the prostate with all beam directions passing through the prostate. An alternative to a phased array is a spherical or parabolic transducer array where the array comprises of a plurality of small transducers mounted on a curved surface and radiating into the body from different directions, always keeping the target tissue (such as prostate or cancer) in focus. Another alternative is focusing the ultrasound with a lens. Similar procedure can be used for treating emphysema. The advantage of ultrasound is the much smaller focused spot, but it normally requires immersion of the patient in a water bath unless an ultrasonic impedance match coating is used over the skin of the patient.

Clearly a moving transmitter can be replaced by an array of fixed transmitters aiming at the target tissue from different direction, however a large number of fixed transmitters are needed to get the benefit of a single moving one. The principle of heating the target tissue more than the surrounding tissue still applies, as the target tissue will be heated by all transmitters while the adjacent tissue will be heated by one, or a few, transmitters. The common element is all the different embodiments is having a high intensity focused energy beam arriving from different angular directions, all said directions passing through the non-desired, or malignant, tissue. The different angular directions can be achieved by scanning, by a plurality of transducers, or a combination or both.

A test was conducted on a rat, comparing the heating of a healthy lung to the same lung without the blood flow (to simulate emphysema). The blood flow was stopped by killing the rat. The body of the live rat was placed between two metal electrodes, about 3×3 cm each. The rat was anesthetized using urethane. A miniature thermocouple was inserted into the lung via a cut in the trachea. The electrodes were impedance matched to a 2 W 10 MHz RF generator with an output impedance of 50 Ohm. The matching was done via an L-pad (inductor in series and capacitor in parallel to the rat). The values of the inductor and capacitor were computed for the specific rat by using a standard L-matching formula. The body temperature of the rat was 38° C. After about 2 minutes of RF the temperature stabilized at about 39° C. and did not increase further. At this point the rat was killed by an injection of urethane and the experiment repeated. After 2 minutes the temperature increased about 3° C., and stabilized at an increase of about 4° C. after about 5 minutes. The temperature was not constant because the rat was dead, but the increase in lung temperature caused by the RF heating was repeatable and was about 4 times the increase when blood was flowing (after correcting for the cooling effect of the room). In this experiment the energy source was not scanning. With a scanning source the RF power could have been raised by about fourfold, assuming the dwell time on the tissue outside the lung is under 25%. This provides a 4×4=16:1 heating ratio. Assuming the surrounding tissue can only be heated by 2-3 degrees (say from 37° to 39° or 40° in humans), the parts of the lung with emphysema can be heated by 32°-48°, reaching 69° to 85°.

What is claimed is:

1. A method for treating emphysema, the method comprising of:

providing a source of microwave radiation, focusing the microwave radiation to form a focused spot, aiming the focused spot onto a lung of a patient affected by emphysema, the lung comprising healthy and non-healthy areas of lung tissue, the healthy areas having higher rates of blood flow than the non-healthy areas, moving the source of microwave radiation along a path around the body of the patient while the patient is breathing, while aiming the focused spot onto the lung, continuing to aim the focused spot onto the lung until at least a portion of the non-healthy areas reaches at least a first temperature while allowing the higher rates of blood flow in the healthy areas to carry away heat from the healthy areas and thereby prevent the healthy areas from exceeding a second temperature, lower than the first temperature, wherein the first temperature is at least 50 degrees Celsius and the second temperature is no more than 45 degrees Celsius.

2. The method as in claim 1 wherein the focused spot is larger than some of the non-healthy areas.

3. The method as in claim 1 further comprising temporarily collapsing the lung.

4. The method as in claim 1 wherein the microwave radiation has a frequency of approximately 2.45 GHz.

5. The method as in claim 1 wherein the power of the microwave radiation is lower than the power necessary for ablation of the non-healthy areas, and wherein the method further comprises measuring reflection or absorption of the microwave radiation for imaging.

6. The method as in claim 1 wherein the first temperature is at least 60 degrees C.

7. The method as in claim 1 further comprising administering chilled air to the patient for breathing while aiming the focused spot onto the lung.

8. The method as in claim 1 further comprising coating at least part of the skin of the patient with an impedance matching coating for reducing reflection of microwave energy.

9. The method as in claim 1 wherein the path of the source of microwave radiation allows the focused spot to be continuously aimed onto the lung without the microwave radiation passing through sensitive organs of the patient.

10. The method as in claim 9 wherein the sensitive organs include the head, the heart, and the spine.

11. The method as in claim 1 wherein the microwave radiation has a frequency of approximately 915 Mhz.

12. The method as in claim 1 further comprising using an apodizing plate to shape the microwave radiation.

* * * * *